(12) United States Patent
Sugo et al.

(10) Patent No.: US 6,547,740 B2
(45) Date of Patent: Apr. 15, 2003

(54) BLOOD PRESSURE MONITORING APPARATUS

(75) Inventors: Yoshihiro Sugo, Tokyo (JP); Rie Tanaka, Tokyo (JP); Mitsushi Hyogo, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 7 days.

(21) Appl. No.: 09/855,565

(22) Filed: May 16, 2001

(65) Prior Publication Data

US 2002/0002339 A1 Jan. 3, 2002

(30) Foreign Application Priority Data

May 16, 2000 (JP) ........................................ 2000-142759

(51) Int. Cl.[7] ................................................. A61B 5/02
(52) U.S. Cl. ...................... 600/485; 600/492; 600/490; 600/496
(58) Field of Search ............................... 600/485, 490, 600/492–496

(56) References Cited

U.S. PATENT DOCUMENTS

| 5,564,427 | A | | 10/1996 | Aso et al. .................... 128/681 |
|---|---|---|---|---|
| 5,584,298 | A | * | 12/1996 | Kabal .......................... 128/672 |
| 5,649,543 | A | * | 7/1997 | Hosaka et al. ............... 128/681 |
| 5,791,347 | A | * | 8/1998 | Flaherty et al. .............. 128/672 |
| 5,868,679 | A | * | 2/1999 | Miyazaki ..................... 600/494 |
| 6,027,453 | A | * | 2/2000 | Miwa et al. .................. 600/485 |
| 6,083,171 | A | | 7/2000 | Ono et al. .................... 600/494 |

\* cited by examiner

*Primary Examiner*—Tony M. Argenbright
*Assistant Examiner*—Johnny H. Hoang
(74) *Attorney, Agent, or Firm*—Sughrue Mion, PLLC

(57) ABSTRACT

A blood pressure monitoring apparatus includes a blood pressure measuring device for measuring blood pressure employing a cuff, a pulse wave propagation time measuring device for measuring the pulse wave propagation time, a hemodynamics measuring device for measuring the hemodynamics, and a control device for controlling the blood pressure measuring device on the basis of a change in pulse wave propagation time measured by the pulse wave propagation time measuring device and a change in hemodynamics measured by the hemodynamics measuring device. The control device controls the blood pressure measuring device to measure the blood pressure on the basis of the amount of change and change trend in the pulse wave propagation time measured by the pulse wave propagation time measuring device, and the amount of change and change trend in the hemodynamics measured by the hemodynamics measuring device.

8 Claims, 3 Drawing Sheets

BLOOD PRESSURE MONITORING APPARATUS

BACKGROUND OF INVENTION

1. Field of Invention

The present invention relates to a blood pressure monitoring apparatus used in the fields where the continuous blood monitoring for the patient is required in the operation room, the intensive care unit, the emergency treatment room, or the artificial dialysis treatment room.

2. Related Art

Conventionally, the blood pressure monitoring apparatus for monitoring the blood pressure of the subject by measuring the blood pressure of the subject continuously is well known in which a cuff is wound around an upper arm portion or the like of the subject to make the noninvasive blood pressure measurement by an oscillometric method, or the artery of the subject is punctured to make the invasive blood pressure measurement.

By the way, the conventional blood pressure monitoring apparatus had the following disadvantages.

That is, (a) the blood pressure monitoring apparatus for making the noninvasive blood pressure measurement with the cuff often left unnoticed a sudden change in blood pressure due to a shock, when the measurement interval was long, for example, five minutes or more, in the periodic NIBP measurement. To cope with this situation, the measurement interval may be shortened to one minute, for example, to lessen the oversights of sudden change in blood pressure. However, when the measurement interval is shorter, some load may be exerted on the portion with the cuff wound.

(b) in the periodic NIBP measurement, the patient may undergo frequent tightness of the cuff with pressure more than necessary.

And (c) with the blood pressure monitoring apparatus for making the invasive blood pressure measurement, the subject may be spiritually affected by the invasion. Also, it takes more time than the noninvasive blood pressure measurement, and imposes more burden on the medical stuff.

SUMMARY OF INVENTION

Thus, it is an object of the present invention to provide a blood pressure monitoring apparatus that can monitor the blood pressure safely and with high accuracy in continuous manner, without giving load on the subject.

According to a first aspect of the present invention, there is provided a blood pressure monitoring apparatus comprising blood pressure measuring means for measuring the blood pressure employing a cuff, pulse wave propagation parameter measuring means for measuring the pulse wave propagation parameter, hemodynamics measuring means for measuring the hemodynamics, and control means for controlling the blood pressure measuring means on the basis of a change in pulse wave propagation parameter measured by the pulse wave propagation parameter measuring means and a change in hemodynamics measured by hemodynamics measuring means, wherein the control means controls the blood pressure measuring means to measure the blood pressure on the basis of the amount of change and discriminated change trend in the pulse wave propagation parameter measured by the pulse wave propagation parameter measuring means, and the amount of change and discriminated change trend in the hemodynamics measured by the hemodynamics measuring means.

According to a second aspect of the invention, there is provided the control means controls the blood pressure measuring means on the basis of a comparison between a pulse wave propagation parameter change threshold memorized to monitor the amount of change in the pulse wave propagation parameter and the amount of change in the pulse wave propagation parameter measured by the pulse wave propagation parameter measuring means and a comparison between a hemodynamics change threshold memorized to monitor the amount of change in the hemodynamics and the amount of change in the hemodynamics measured by the hemodynamics measuring means.

According to a third aspect of the invention, there is provided the blood pressure monitoring apparatus, wherein the control means updates the pulse wave propagation parameter change threshold.

According to a fourth aspect of the invention, there is provided a blood pressure monitoring apparatus comprising blood pressure measuring means for measuring the blood pressure employing a cuff, pulse wave propagation parameter measuring means for measuring the pulse wave propagation parameter, hemodynamics measuring means for measuring the hemodynamics, and control means for controlling the blood pressure measuring means on the basis of a change in pulse wave propagation parameter measured by the pulse wave propagation parameter measuring means and a change in hemodynamics measured by the hemodynamics measuring means, wherein the control means compares between a pulse wave propagation parameter change threshold memorized to monitor the amount of change in pulse wave propagation parameter and the amount of change in pulse wave propagation parameter measured by the pulse wave propagation parameter measuring means and detect the change trend in the measured pulse wave propagation parameter, compares between a hemodynamics change threshold memorized to monitor amount of the change in the hemodynamics and the amount of change in hemodynamics measured by the hemodynamics measuring means, detects the change trend in the hemodynamics measured, and updates the pulse wave propagation parameter change threshold on the basis of the results of two comparisons with the thresholds and the detected change trends.

According to a fifth aspect of the invention, there is provided the blood pressure monitoring apparatus, wherein the control means controls the blood pressure measuring means to measure the blood pressure on the basis of a comparison between the updated pulse wave propagation parameter change threshold and the pulse wave propagation parameter measured by the pulse wave propagation parameter measuring means.

Further, according to a sixth aspect of the invention, there is provided the blood pressure monitoring apparatus, wherein the hemodynamics measuring means measures at least one of a heart rate, a pulse wave amplitude, and a DC component of pulse wave, and the control means controls the blood pressure measuring means on the basis of at least one of the heart rate measured, the pulse wave amplitude, and the DC component of pulse wave.

Furthermore, according to a seventh aspect of the invention, there is provided the blood pressure monitoring apparatus, wherein the control means controls the blood pressure measuring means on the basis of a pulsation rate fluctuation rate calculated from the changes in the amplitude of pulse wave and the DC component of pulse wave measured by hemodynamics measuring means.

And according to an eighth aspect of the invention, there is provided the blood pressure monitoring apparatus, wherein the control means updates the pulse wave propagation parameter change threshold on the basis of at least one of the change in pulse wave propagation parameter, the change in heart rate, and the pulsation rate fluctuation rate.

DETAILED DESCRIPTION OF PREFERRED EMBODIMENTS

A fundamental idea of this invention is as follows.

Figure 3:
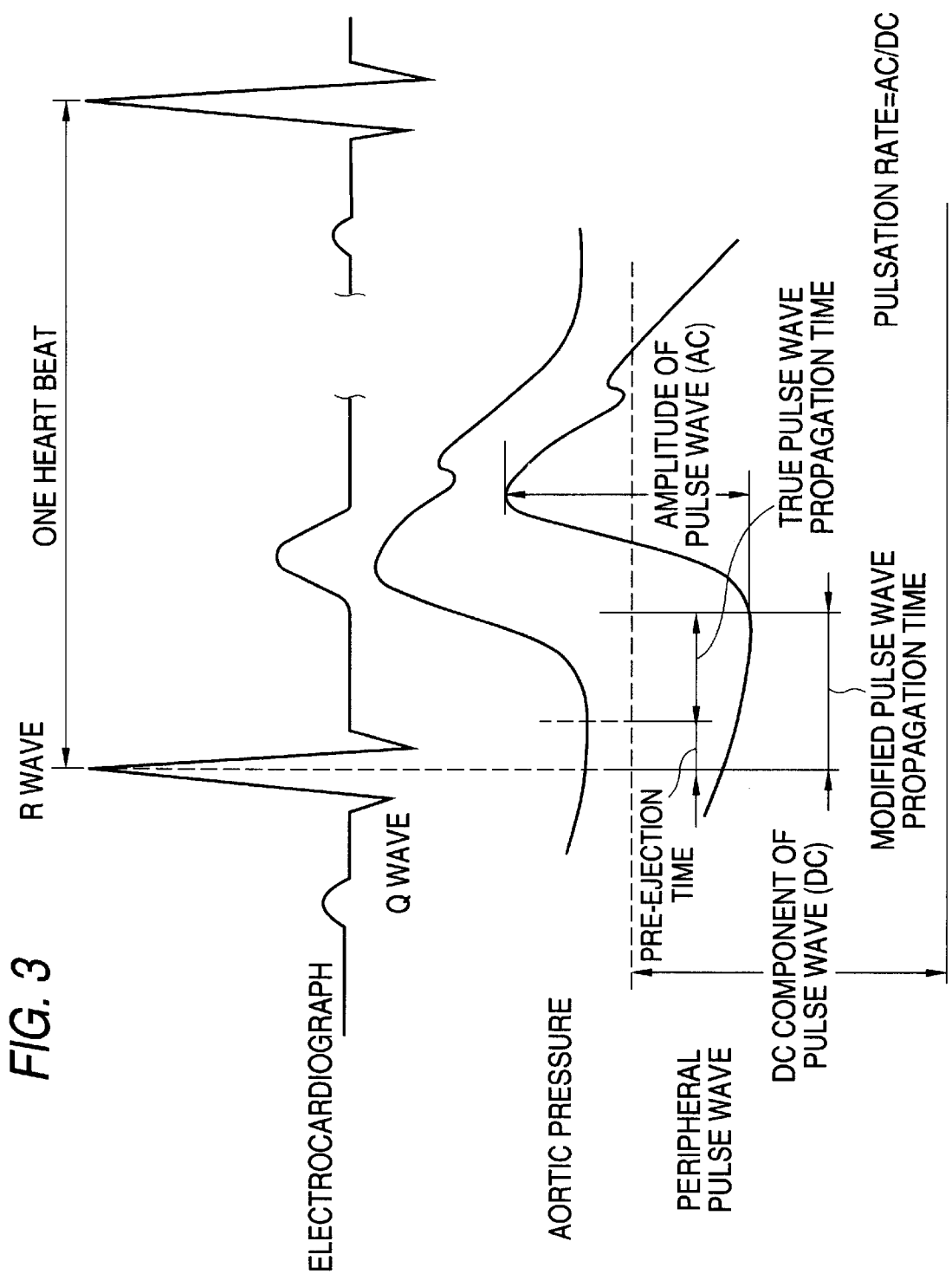
FIG. 3 is a waveform chart for explaining the pulse wave propagation time for measurement in the blood pressure monitoring apparatus according to the invention.

One method for the blood pressure monitoring apparatus for making the noninvasive blood pressure measurement involves measuring the blood pressure using the pulse wave propagation velocity (pulse wave propagation time for fixed distance). A principal for measuring the blood pressure from this pulse wave propagation velocity is as follows. That is, a specific point of pulse wave appears at later time than the specific point of aorta wave in the peripheral blood vessel side for the fingers or ears for example, as shown in FIG. 3. This delay time is the pulse wave propagation time. And the pulse wave propagation velocity corresponding to the pulse wave propagation time for fixed distance is represented as a function of the volumetric elasticity of blood vessel, and if the blood pressure increases, the volumetric elasticity of blood vessel increases, the blood vessel wall is hardened, and the propagation velocity becomes fast.

Accordingly, the fluctuation of blood pressure can be obtained from the pulse wave propagation velocity. And the fluctuation of blood pressure of the subject can be monitored by measuring the pulse wave propagation time successively. In this case, the amount of change ΔT in pulse wave propagation time exceeds a predetermined change threshold ΔTs of pulse wave propagation time, it is judged that the subject has a sudden change in blood pressure, at which point the noninvasive blood pressure measurement with the cuff may be performed.

However, it is well known that the relation between the pulse wave propagation time (PWTT) and the blood pressure which is obtained from the electrocardiograph and the pulse wave of peripheral blood vessel may be affected by the change in pre-ejection period (PEP) of heart contained in the pulse wave propagation time (which is defined as the modified pulse wave propagation time). That is, the modified pulse wave propagation time can be generally obtained by the following expression.

Modified pulse wave propagation time=(pre-ejection period)+(true pulse wave propagation time)  (1)

The pre-ejection period represents the cardiac systole time, or the time from the start of systole in the left ventricle (corresponding to the Q wave in the electrocardiograph) to the opening of the aortic valve (corresponding to the occurrence of aortic pressure). Accordingly, the autonomic response of the heart such as a change in myocardial contractibility has actually a great effect on the pre-ejection period. For example, if the myocardial contractibility is increased, the pre-ejection period is shortened. This phenomenon makes the modified pulse wave propagation time short. On the contrary, if the myocardial contractibility is decreased, the pre-ejection period is lengthened, whereby the modified pulse wave propagation time is lengthened.

The start of pre-ejection period medically means the Q wave, but because the R wave is convenient in measurement and detection of the electrocardiograph, the R wave may be considered as the start of pre-ejection period.

Thus, this invention has a feature that the noninvasive blood pressure measurement with the cuff is made with high accuracy by eliminating the influence on the pre-ejection period contained in the modified pulse wave propagation time.

On one hand, the blood pressure can be represented by a product of the cardiac output and the Systemic Vascular Resistance in accordance with the following expression.

Blood pressure (average blood pressure)=(cardiac output)×(Systemic Vascular Resistance)  (2)

Herein, the relation between the pulse wave propagation time and the hemodynamics change when the cardiac output and the Systemic Vascular Resistance are changed individually and the blood pressure is correspondingly changed is as follows.

The low blood pressure due to the cardiac sympathetic suppression or the like acts to lengthen the true pulse wave propagation time, and to lengthen the pre-ejection period because of the decreased myocardial contractibility. Consequently, owing to their stimulus effect, the modified pulse wave propagation time is further increased. In this case, the conditions of the subject (patient) may be recognized more surely by increasing the pulse wave propagation time change threshold based on the hemodynamic waveform change of pulse wave associated with the decreased heart rate or cardiac output accompanied by the cardiac sympathetic suppression.

On the other hand, the high blood pressure caused by the increased cardiac output due to the cardiac sympathetic stimulus or the like acts to shorten the true pulse wave propagation time directly, and also shortens the pre-ejection period due to the increased myocardial contractibility. Consequently, owing to their stimulus effect, the modified pulse wave propagation time is further decreased. In this case, the conditions of the subject (patient) may be recognized more surely by increasing the pulse wave propagation time change threshold, based on the hemodynamic waveform change of pulse wave associated with the increased heart rate or cardiac output accompanied by the cardiac sympathetic stimulus.

The biological body has a function of baroreceptor (blood pressure reflex). This is a reflex system for monitoring the change in blood pressure and reducing the width of change in blood pressure, or momentarily sensing increase or decrease in blood pressure, if any, and relieve the fluctuation in blood pressure. That is, if the blood pressure fluctuates, the blood pressure reflex system acts to keep the blood pressure at a certain level.

Thus, the low blood pressure caused by the dilation of blood vessel directly acts to lengthen the true pulse wave propagation time, but acts to shorten the pre-ejection period because the myocardial contractibility is increased owing to the baroreceptor. Consequently, their antagonistic effect occurs to keep the modified pulse wave propagation time from increasing. In this case, the conditions of the subject (patient) may be recognized more surely by shortening the pulse wave propagation time change threshold, based on the hemodynamic waveform change of pulse wave associated with the reflective increase in heart rate or the dilation of blood vessel.

Also, the high blood pressure caused by the constriction of blood vessel directly acts to shorten the true pulse wave propagation time, but acts to lengthen the pre-ejection period because the myocardial contractibility is decreased owing to the baroreceptor. Consequently, their antagonistic effect occurs to keep the modified pulse wave propagation time from decreasing. In this case, the conditions of the subject (patient) may be recognized more surely by shortening the pulse wave propagation time change threshold, based on the hemodynamic waveform change of pulse wave associated with the reflective decrease in heart rate or the constriction of blood vessel, in the same way as described above.

Next, there will be described some instances of (1) hemodynamic waveform change of pulse wave associated with the decrease in cardiac output, (2) hemodynamic waveform change of pulse wave associated with the increase in cardiac output, (3) hemodynamic waveform change of pulse wave associated with the dilation of blood vessel, and (4) hemodynamic waveform change of pulse wave associated with the constriction of blood vessel.

(a) Amplitude of Pulse Wave

The decreased cardiac output gives rise to the decrease in peripheral blood flow. Therefore, the amplitude of pulse wave decreases.

The increased cardiac output gives rise to the increase in peripheral blood flow. Therefore, the amplitude of pulse wave increases.

Due to the constriction or dilation of blood vessel, the vascular compliance is varied. This vascular compliance can be represented in the following expression.

Vascular compliance=(change in volume of blood vessel)/(pulse pressure)  (3)

Herein, the pulse pressure is a difference between the systolic pressure and the diastolic pressure.

Since the volume of blood vessel is varied due to a change in vascular compliance, the amplitude of pulse wave has a change as follows.

The dilation of blood vessel increases the vascular compliance. Therefore, the amplitude of pulse wave increases.

The constriction of blood vessel decreases the vascular compliance. Therefore, the amplitude of pulse wave decreases.

(b) DC Component of Pulse Wave

The decreased or increased peripheral blood flow or the constriction or dilation of blood vessel changes the diameter of blood vessel, and thereby changing the amount of blood flow. The photoelectric pulse wave is obtained by detecting the remaining amount of transmitted light in which the amount of light absorbed by the tissue or blood is removed from the light irradiated from the skin surface. Therefore, the amount of transmitted light is varied by the change in the absorbed amount of light caused by the change in diameter of blood vessel, so that the DC component of pulse wave is changed.

The decreased cardiac output gives rise to the decrease in peripheral blood flow. Therefore, the absorbed amount of light is decreased and the amount of transmitted light is increased, so that the DC component of pulse wave is increased.

The increased cardiac output gives rise to the increase in peripheral blood flow. Therefore, the absorbed amount of light is increased and the amount of transmitted light is decreased, so that the DC component of pulse wave is decreased.

The dilation of blood vessel gives rise to the increase in diameter of blood vessel. Therefore, the absorbed amount of light is increased and the amount of transmitted light is decreased, so that the DC component of pulse wave is decreased.

The constriction of blood vessel gives rise to the decrease in diameter of blood vessel. Therefore, the absorbed amount of light is decreased and the amount of transmitted light is increased, so that the DC component of pulse wave is increased.

(c) Pulsation Rate of Pulse Wave

The pulsation rate can be obtained as the ratio of the amplitude of photoelectric pulse wave and the DC component in accordance with the following expression (see FIG. 3).

Pulsation rate=(amplitude AC of photoelectric pulse wave)/(DC component DC of photoelectric pulse wave)  (4)

The decreased cardiac output decreases the amplitude of pulse wave, and increases the DC component of pulse wave, so that the pulsation rate is decreased.

The increased cardiac output increases the amplitude of pulse wave, and decreases the DC component of pulse wave, so that the pulsation rate is increased.

The dilation of blood vessel increases the amplitude of pulse wave, and decreases the DC component of pulse wave, so that the pulsation rate is increased.

The constriction of blood vessel decreases the amplitude of pulse wave, and increases the DC component of pulse wave, so that the pulsation rate is decreased.

Note that the pulsation rate fluctuation rate acdc indicating the fluctuation of the pulsation rate (AC/DC) can be obtained in accordance with the following expression (see FIG. 3).

$$acdc=\{(AC2/DC2)-(AC1/DC1)\}/(AC1/DC1) \quad (5)$$

The relation of the hemodynamic waveforms of pulse wave associated with the changes in cardiac output or diameter of blood vessel is listed in Table 1 as below.

TABLE 1

|  | Blood pressure | Pulse wave propagation time F1 | Heart rate F2 | Amplitude of pulse wave | DC component of pulse wave | Pulsation rate F3 |
| --- | --- | --- | --- | --- | --- | --- |
| Decrease in myocardial contractibility | decrease | Remarkably increase | decrease | decrease | increase | decrease |
| Increase in myocardial | increase | Remarkably decrease | increase | increase | decrease | increase |

TABLE 1-continued

| | Blood pressure | Pulse wave propagation time F1 | Heart rate F2 | Amplitude of pulse wave | DC component of pulse wave | Pulsation rate F3 |
|---|---|---|---|---|---|---|
| contractibility | | | | | | |
| Dilation of blood vessel | decrease | Slightly increase | increase | increase | decrease | increase |
| Constriction of blood vessel | increase | Slightly decrease | decrease | decrease | increase | decrease |

Preferred Embodiments

The preferred embodiments of a blood pressure monitoring apparatus according to the present invention will be described below with reference to the accompanying drawings.

(A) Constitution of Blood Pressure Monitoring Apparatus

Figure 1:
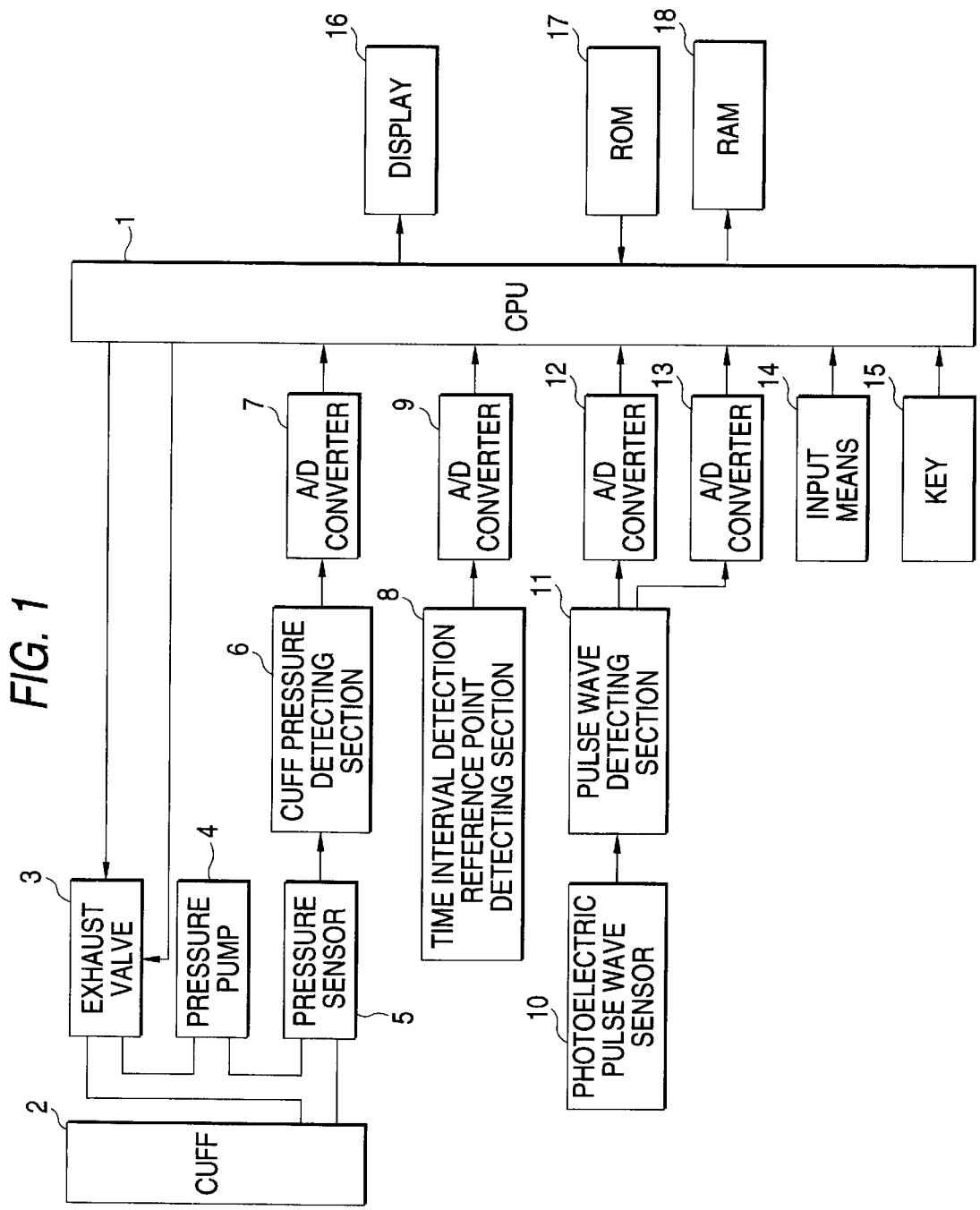
FIG. 1 is a block diagram of the schematic system configuration showing one example of a blood pressure monitoring apparatus according to the present invention.

FIG. 1 is a block diagram of the system configuration showing one example of the blood pressure monitoring apparatus according to the present invention. In FIG. 1, a cuff 2 is provided. This cuff 2 is attached on an upper arm portion or a finger of the subject, and has its interior opened or enclosed to or from the atmosphere via an exhaust valve 3. This cuff 2 is supplied with the air by a pressure pump 4, and has a pressure sensor 5 mounted on a main body of the cuff 2, an output of this sensor 5 being detected by a cuff pressure detecting section 6. And an output of this cuff pressure detecting section 6 is converted into a digital signal by an A/D converter 7 and input as the blood pressure measurement data into a CPU (Central Processing Unit) 1.

Also, a time interval detection reference point detecting section 8 is provided. This time interval detection reference point detecting section 8 is configured to detect the time point when the R wave arises in the electrocardiograph. An output of this detecting section 8 is converted into a digital signal by an A/D converter 9, and input as the time interval detection reference point detecting data into the CPU (Central Processing Unit) 1. Also, this detecting section 8 comprises an electrode attached on a chest portion of the subject and an electrocardiograph R wave detecting section connected to this electrode. Alternately or in addition to above configuration, this detecting section 8 may comprise a pressure pulse wave sensor for sensing the pulse wave of the aorta to detect the time point at which the aortic pressure reaches a bottom value.

Further, a photoelectric pulse wave sensor 10 is provided. This photoelectric pulse wave sensor 10 is attached on a finger of the subject, for example, and configured to measure the pulse wave on the side of the peripheral blood vessel. An output of this photoelectric pulse wave sensor 10 is transferred to the pulse wave detecting section 11 to detect the pulse wave in a region of the subject where the sensor is attached. And the pulse wave detecting section 11 outputs the AC component and the DC component of pulse wave separately. Then, the AC component of pulse wave is converted into the digital signal by the A/D converter 12, and input as the AC component data into the CPU 1. Also, the DC component of pulse wave is converted into the digital signal by the A/D converter 13, and input as the DC component data of pulse wave into the CPU 1.

On the other hand, input means 14 is provided. This input means 14 is configured to input an initial pulse wave propagation time change threshold ΔTs and the initial hemodynamics change thresholds ΔHRS, r1s, r2. In this case, the initial hemodynamics change thresholds ΔHRS is a value corresponding to the change in heart rate, r1s is a value corresponding to the fluctuation rate in amplitude of pulse wave in the peripheral blood vessel, and r2 is a threshold update ratio.

And a key 15 is provided. This key 15 is employed to measure the blood pressure with the cuff 2 by manual operation. Also, the CPU 1 executes a predetermined processing program on the basis of a signal given from the A/D converters 7, 9, 12 and 13 and the key 15, to output a required control signal to the exhaust valve 3 and the pressure pump 4, and pass the processed result to a display 16. A ROM 17 connected to the CPU 1 stores the predetermined processing program. And a RAM 18 has the set values of various registers and various data areas for storing the blood pressure measurement data and so on.

The following registers are set.

RT1: register for storing the pulse wave propagation time T1.
RT2: register for storing the pulse wave propagation time T2.
RHT1: register for storing the heart rate HR1.
RHT2: register for storing the heart rate HR2.
RAC1: register for storing the amplitude AC1 of pulse wave in the peripheral blood vessel.
RAC2: register for storing the amplitude AC2 of pulse wave in the peripheral blood vessel.
RDC1: register for storing the DC component DC1 of pulse wave in the peripheral blood vessel.
RDC2: register for storing the DC component DC2 of pulse wave in the peripheral blood vessel.
Racdc1: register for storing the pulsation rate acdc1 of pulse wave in the peripheral blood vessel.
Racdc2: register for storing the pulsation rate acdc2 of pulse wave in the peripheral blood vessel.

The cuff 2, the exhaust valve 3, the pressure pump 4, the pressure sensor 5, the cuff pressure detecting section 6 and the A/D converter 7 constitute blood pressure measuring means. Also, the RAM 18 corresponds to memorizing means. Further, the time interval detection reference point detecting section 8, the A/D converter 9 and the CPU 1 constitute pulse wave propagation time measuring means. And the photoelectric pulse wave sensor 10, the pulse wave detecting section 11, the A/D converters 12, 13 and the CPU 1 constitute hemodynamics measuring means. Note that the CPU 1 corresponds to control means.

(B) Operation of Blood Pressure Monitoring Apparatus

Figure 2:
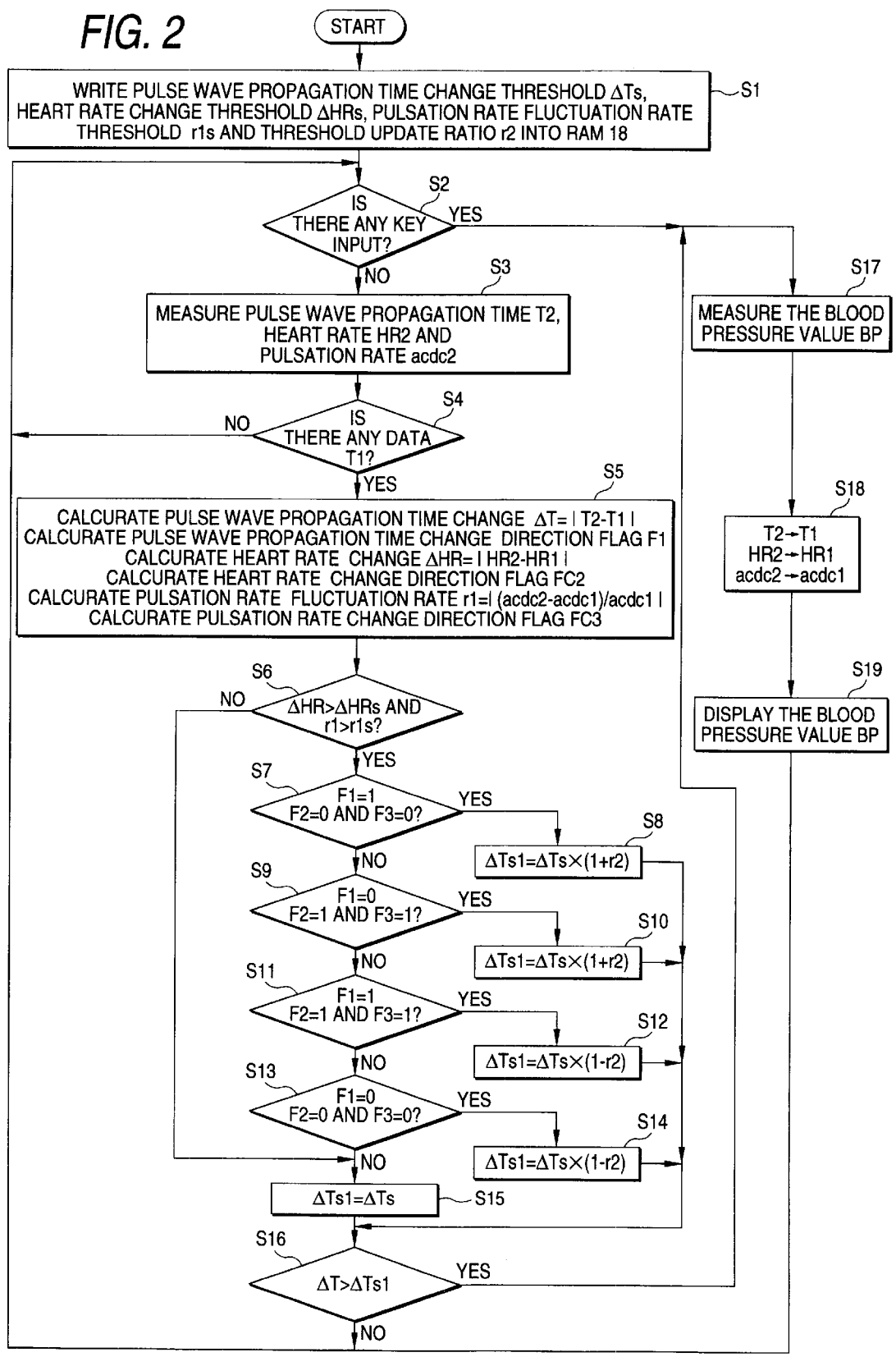
FIG. 2 is a flowchart showing the operation of the blood pressure monitoring apparatus according to the invention.

Referring to FIGS. 1 and 2, the operation of the blood pressure monitoring apparatus according to the invention with the above system configuration will be described below. FIG. 2 is a flowchart showing the operation of the blood pressure monitoring apparatus according to the invention.

At step S1, the pulse wave propagation time change threshold ΔTs, the heart rate change threshold ΔHRS, the pulsation rate fluctuation rate threshold r1s, and the threshold update ratio r2 are input by the input means 14, and written into the RAM 18. Note that the data regarding these thresholds ΔTs, ΔHRS, r1s and r2 are determined beforehand by the body weight and height of the subject.

At step S2, a determination is made whether or not there is any input by the key 15. If there is the input by the key 15, at step 17, the blood pressure of the subject is measured employing the cuff 2 while the exhaust valve 3 and the pressure pump 4 are controlled by the CPU 1. At this time, the blood pressure measurement data input from the A/D converter 7 is processed inside the CPU 1, and a blood pressure value BP measured by the oscillometric method is written into the RAM 18.

Thereafter, at step S18, the data regarding the pulse wave propagation time T2 stored in a register RT2 is transferred to a register RT1, the data regarding the heart rate HR2 stored in a register RHR2 is transferred to a register RHR1, and the data regarding the pulsation rate acdc2 stored in a register Racdc2 is transferred to a register Racdc1. In this case, unless the measurement process of the pulse wave propagation time T2 is performed, the transfer of the data to the registers RT1, RHR1 and Eacdc1 is substantially not performed. After the transfer process of the data between registers is performed, at step S19, the blood pressure value BP measured in advance is displayed on the display 16. Then the routine returns to step S2.

At step S2 again, a determination is made whether or not there is any input by the key 15. If there is no input by the key 15, the pulse wave propagation time 12 which corresponds to the period from the time when the aortic pressure reaches the bottom value to the time when the pulse wave on the peripheral blood vessel side reaches the bottom value is measured on the basis of the data from the A/D converters 9 and 12 at almost the same time as the occurrence of the R wave in the electrocardiograph at step S3. That measurement data is stored in the register RT2 of the RAM 18. Further, the pulsation rate of pulse wave in the peripheral blood vessel is measured. These measurement data are stored in the registers RHR2 and Racdc2.

At step S4, a determination is made whether or not there is any data regarding the pulse wave propagation time T1. If there is any data, the pulse wave propagation time change ΔT and a pulse wave propagation time change trend flag F1, the heart rate change ΔHR and a heart rate change trend flag F2, and the pulsation rate fluctuation rate r1 and a pulsation rate fluctuation direction flag F3 are calculated in accordance with the following expressions at step S5. Namely by using flag F1 to F3, a change in trend of each parameter is discriminated whether increase or decreasing.

$$\Delta T = |T2 - T1| \tag{6}$$

F1=1 for T2−T1≧0
F1=0 for T2−T1<0

$$\Delta HR = |HR2 - HR1| \tag{7}$$

F2=1 for HR2−HR1≧0
F2=0 for HR2−HR1<0

$$r1 = |(acdc2 - acdc1)/acdc1| \tag{8}$$

F3=1 for acdc2−acdc1≧0
F3=0 for acdc2−acdc1<0

At step S6, a determination is made whether or not the heart rate change ΔHR obtained at step S5 exceeds the heart rate change threshold ΔHRS input beforehand, and whether or not the pulsation rate fluctuation rate r1 is beyond the pulsation rate fluctuation rate threshold r1s input beforehand. That is ΔHR>ΔHRS, and r1>r1s are examined. If these conditions are not satisfied, the routine passes to step S15.

If the above conditions are satisfied at step S6, each flag is judged. And the pulse wave propagation time change threshold ΔTs is updated in accordance with a result of the judge, and the updated pulse wave propagation time change threshold ΔTs1 is obtained.

At step S7, a determination is made whether or not the flags satisfy the conditions of F1=1, F2=0 and F3=0. And if the conditions are satisfied, the updated pulse wave propagation time change threshold ΔTs1 is calculated in accordance with the following expression at step S8.

$$\Delta Ts1 = \Delta Ts \times (1 + r2) \tag{9}$$

In this case, the pulse wave propagation time change threshold is updated to be larger by the threshold update ratio r2. This is made with the background of a decrease in myocardial contractibility in the Table 1. Remarkable increase in the pulse wave propagation time and a decrease in blood pressure are recognized, by detecting a decrease in heart rate and pulsation rate and the pulse wave propagation time change threshold is updated in a greater direction. Note that if the above conditions are not satisfied, the routine transfers to step S9.

At step S9, a determination is made whether or not the flags satisfy the conditions of F1=0, F2=1 and F3=1. And if the conditions are satisfied, the updated pulse wave propagation time change threshold ΔTs1 is calculated in accordance with the following expression at step S10.

$$\Delta Ts1 = \Delta Ts \times (1 + r2) \tag{10}$$

In this case, the pulse wave propagation time change threshold is updated to be larger by the threshold update ratio r2. This is made with the background of an increase in myocardial contractibility in the Table 1. Remarkable decrease in the pulse wave propagation time and an increase in blood pressure are recognized by detecting an increase in heart rate and pulsation rate and the pulse wave propagation time change threshold is updated in a greater direction. Note that if the above conditions are not satisfied, the routine transfers to step S11.

At step S11, a determination is made whether or not the flags satisfy the conditions of F1=1, F2=1 and F3=1. And if the conditions are satisfied, the updated pulse wave propagation time change threshold ΔTs1 is calculated in accordance with the following expression at step S12.

$$\Delta Ts1 = \Delta Ts \times (1 - r2) \tag{11}$$

In this case, the pulse wave propagation time change threshold is updated to be smaller by the threshold update ratio r2. This is made with the background of a dilation of blood vessel in the Table 1. Slightly increase in the pulse wave propagation time and a decrease in blood pressure are recongnized by detecting an increase in heart rate and pulsation rate and the pulse wave propagation time change threshold is updated in a smaller direction. Note that if the above conditions are not satisfied, the routine transfers to step S13.

At step S13, a determination is made whether or not the flags satisfy the conditions of F1=0, F2=0 and F3=0. And if the conditions are satisfied, the updated pulse wave propagation time change threshold ΔTs1 is calculated in accordance with the following expression at step S14.

$$\Delta Ts1 = \Delta Ts \times (1 - r2) \tag{12}$$

In this case, the pulse wave propagation time change threshold is updated to be smaller by the threshold update ratio r2. This is made with the background of a constriction of blood vessel in the Table 1, Slightly decrease in the pulse wave propagation time and an increase in blood pressure are recognized by detecting a decrease in heart rate and pulsation rate and the pulse wave propagation time change threshold is updated in a smaller direction. Note that if the above conditions are not satisfied, the routine transfers to step S15.

At step S15, the updated pulse wave propagation time change threshold $\Delta Ts1$ is obtained in accordance with the following expression.

$$\Delta Ts1 = \Delta Ts \qquad (13)$$

In this case, the pulse wave propagation time change threshold is not updated.

After the updated pulse wave propagation time change threshold $\Delta Ts1$ is obtained in the above way, it is determined at step S16 whether or not the pulse wave propagation time change $\Delta T$ is beyond the updated pulse wave propagation time change threshold $\Delta Ts1$ in accordance with the following expression.

$$\Delta T > \Delta Ts1 \qquad (14)$$

If the above condition is met at step S16, considering that there is a sudden change in blood pressure of the subject due to a shock or the like, the routine transfers to step S17. Note that if the above condition is not met, the routine gets back to step S2 to repeat a series of above operations again.

At step S17, to cope with the sudden change in blood pressure of the subject, the blood pressure measurement is conducted with the cuff 2. And its measured value BP is written into a data area of the RAM 18. And the data regarding the pulse wave propagation time T2 stored at the register RT2 in the RAM 18 is passed to the register RT1. Also, the data regarding the heart rate HR2 stored in the register RHR2 is passed to the register RHR1, and the data regarding the pulsation rate acdc2 stored in the register Racdc2 is passed to the register Racdc1 at step S18. After the data are passed between the registers, the blood pressure value BP measured in advance is displayed on the display 16. Then the routine gets back to step S2.

In this way, in the blood pressure monitoring apparatus of this embodiment, the hemodynamics measuring means measures the heart rate, the amplitude of pulse wave in the peripheral blood vessel, and the DC component of pulse wave, and control means updates the pulse wave propagation time change threshold on the basis of the changes in pulse wave propagation time, heart rate, amplitude of pulse wave, DC component of pulse wave, and pulsation rate, makes a comparison between the threshold and the measured pulse wave propagation time change, and controls the blood pressure measuring means based on its result of comparison. Thereby, it is possible to monitor a sudden change in blood pressure of the subject with high accuracy and properly, and significantly relieve the load on the subject in the conventional blood pressure measurement.

And the updated pulse wave propagation time change threshold can be calculated simply by multiplying the pulsation rate fluctuation rate calculated on the basis of the changes in amplitude of pulse wave and DC component of pulse wave which are measured by the hemodynamics measuring means by the current threshold, and adding or subtracting the obtained result to or from the current threshold.

Thus, the preferred embodiments of the invention have been described above, but this invention is not limited to the above embodiments. For example, the objects measured by the hemodynamics measuring means, and the number of objects, and the calculation method of the change may be varied in various other ways, and many modifications in design may be made without departing from the scope or spirit of the invention.

As will be apparent from the description of the above embodiments, a blood pressure monitoring apparatus according to this invention comprises blood pressure measuring means for measuring the blood pressure employing a cuff, pulse wave propagation parameter measuring means for measuring the pulse wave propagation parameter, hemodynamics measuring means for measuring the hemodynamics, and control means for controlling the blood pressure measuring means on the basis of a pulse wave propagation parameter change measured by the pulse wave propagation parameter measuring means and a hemodynamics change measured by the hemodynamics measuring means, wherein the control means controls the blood pressure measuring means to measure the blood pressure on the basis of the amount of change and its change trend (increasing or decreasing) in the pulse wave propagation parameter measured by the pulse wave propagation parameter measuring means, and the amount of change and its change trend (increasing or decreasing) in the hemodynamics measured by the hemodynamics measuring means. In this case, the control means controls the blood pressure measuring means in such a way as to make a comparison between a pulse wave propagation parameter change threshold memorized to monitor the amount of change in the pulse wave propagation parameter and the amount of change in the pulse wave propagation parameter measured by the pulse wave propagation parameter measuring means, and make a comparison between a hemodynamics change threshold memorized to monitor the amount of change in the hemodynamics and the amount of change in the hemodynamics measured by the hemodynamics measuring means, and update the pulse wave propagation parameter change threshold. Therefore, many superior advantages are obtained to monitor the blood pressure of the subject safely and continuously with high accuracy, without giving load on the subject.

What is claimed is:

1. A blood pressure monitoring apparatus comprising:

blood pressure measuring means for measuring a blood pressure employing a cuff;

pulse wave propagation parameter measuring means for measuring a pulse wave propagation parameter;

hemodynamics measuring means for measuring hemodynamics, and control means for controlling said blood pressure measuring means based on a change in the pulse wave propagation parameter measured by said pulse wave propagation parameter measuring means and a change in the hemodynamics measured by said hemodynamics measuring means, wherein said control means controls said blood pressure measuring means to measure the blood pressure based on the amount of change and a change in trend in the pulse wave propagation parameter measured by said pulse wave propagation parameter measuring means, and the amount of change and a change in trend in the hemodynamics measured by said hemodynamics measuring means.

2. The blood pressure monitoring apparatus according to claim 1, wherein a pulse wave propagation parameter change threshold, for monitoring the amount of change in said pulse wave propagation parameter, and a hemodynamics change threshold, for monitoring the amount of change in said hemodynamics, are stored in said control means, and said control means controls said blood pressure measuring means based on a comparison between said pulse wave propagation parameter change threshold and the amount of change in the pulse wave propagation parameter measured by said pulse wave propagation parameter measuring means and a comparison between said hemodynamics change threshold and the amount of change in the hemodynamics measured by said hemodynamics measuring means.

3. The blood pressure monitoring apparatus according to claim 2, wherein said control means updates said pulse wave propagation parameter change threshold.

4. A blood pressure monitoring apparatus comprising:
blood pressure measuring means for measuring a blood pressure employing a cuff;
pulse wave propagation parameter measuring means for measuring a pulse wave propagation parameter;
hemodynamics measuring means for measuring hemodynamics; and
control means for controlling said blood pressure measuring means based on a change in the pulse wave propagation parameter measured by said pulse wave propagation parameter measuring means and a change in the hemodynamics measured by said hemodynamics measuring means,
wherein said control means compares between a pulse wave propagation parameter change threshold that is stored in said control means to monitor an amount of said change in said pulse wave propagation parameter and detect a change in trend in said pulse wave propagation parameter, compares between a hemodynamics change threshold stored in said control means to monitor an amount of change in the hemodynamics, detects a change in trend in said hemodynamics measured, and updates said pulse wave propagation parameter change threshold based on results of the two comparisons with said thresholds and the detected change in trends.

5. The blood pressure monitoring apparatus according to claim 4, wherein said control means controls said blood pressure measuring means to measure the blood pressure based on a comparison between an updated pulse wave propagation parameter change threshold and the pulse wave propagation parameter measured by said pulse wave propagation parameter measuring means.

6. The blood pressure monitoring apparatus according to claim 1, wherein said hemodynamics measuring means measures at least one of a heart rate, a pulse wave amplitude, and a DC component of pulse wave, and said control means controls the blood pressure measuring means based on at least one of said heart rate measured, said pulse wave amplitude, and said DC component of pulse wave.

7. The blood pressure monitoring apparatus according to claim 6, wherein said control means controls the blood pressure measuring means based on a pulsation rate fluctuation rate calculated from changes in amplitude of a pulse wave and the DC component of a pulse wave measured by the hemodynamics measuring means.

8. The blood pressure monitoring apparatus according to claim 3, wherein said control means updates said pulse wave propagation parameter change threshold based on at least one of the change in the pulse wave propagation parameter, a change in a heart rate, and a pulsation rate fluctuation rate.

* * * * *